United States Patent
Tuma

(10) Patent No.: US 10,625,471 B2
(45) Date of Patent: Apr. 21, 2020

(54) METHOD FOR MANUFACTURING CLOSING SYSTEMS FOR HYGIENE ARTICLES, IN PARTICULAR DIAPER CLOSING SYSTEMS

(71) Applicant: GOTTLIEB BINDER GMBH & CO. KG, Holzgerlingen (DE)

(72) Inventor: Jan Tuma, Herrenberg (DE)

(73) Assignee: GOTTLIEB BINDER GMBH & CO. KG, Holzgerlingen (DE)

( * ) Notice: Subject to any disclaimer, the term of this patent is extended or adjusted under 35 U.S.C. 154(b) by 21 days.

(21) Appl. No.: 16/069,645

(22) PCT Filed: Jan. 11, 2017

(86) PCT No.: PCT/EP2017/000029
§ 371 (c)(1),
(2) Date: Jul. 12, 2018

(87) PCT Pub. No.: WO2017/129346
PCT Pub. Date: Aug. 3, 2017

(65) Prior Publication Data
US 2019/0016058 A1 Jan. 17, 2019

(30) Foreign Application Priority Data
Jan. 25, 2016 (DE) .................. 10 2016 000 756

(51) Int. Cl.
*B32B 37/00* (2006.01)
*B29C 65/08* (2006.01)
(Continued)

(52) U.S. Cl.
CPC ........ *B29C 65/086* (2013.01); *A44B 18/0065* (2013.01); *A61F 13/15739* (2013.01);
(Continued)

(58) Field of Classification Search
CPC ... B29C 65/08; B29C 65/086; B29C 65/7894; B29C 66/232; B29C 66/4722;
(Continued)

(56) References Cited

U.S. PATENT DOCUMENTS

| | | |
|---|---|---|
| 2003/0235660 A1 | 12/2003 | Blanchard |
| 2004/0116889 A1 | 6/2004 | Carbone, II et al. |

(Continued)

FOREIGN PATENT DOCUMENTS

| | | |
|---|---|---|
| DE | 196 46 318 | 5/1998 |
| EP | 2 564 822 | 3/2013 |

(Continued)

OTHER PUBLICATIONS

International Search Report (ISR) dated Apr. 5, 2017 in International (PCT) Application No. PCT/EP2017/000029.

*Primary Examiner* — James D Sells
(74) *Attorney, Agent, or Firm* — Wenderoth, Lind & Ponack, L.L.P.

(57) ABSTRACT

A method is for manufacturing closing systems for hygiene articles, in particular diaper closing systems. An attachment part (16) is fed to the rear face of a substrate part (18) having protruding closing elements (22) arranged in rows at a predefined distance from each other, and is joined to the substrate part (18) along welding points using an ultrasonic welding process. At least some of the welding points are introduced to extend along weld seam lines (46) between adjoining rows of closing elements (22) and to extend at least partially in parallel to the rows of closing elements (22).

13 Claims, 4 Drawing Sheets

(51) Int. Cl.
  *A61F 13/62* (2006.01)
  *A44B 18/00* (2006.01)
  *A61F 13/15* (2006.01)
  *B29C 65/78* (2006.01)
  *B29C 65/00* (2006.01)
  *B29L 31/48* (2006.01)
  *B29L 31/00* (2006.01)

(52) U.S. Cl.
  CPC ...... *A61F 13/15756* (2013.01); *A61F 13/622* (2013.01); *A61F 13/625* (2013.01); *B29C 65/08* (2013.01); *B29C 65/7894* (2013.01); *B29C 66/1122* (2013.01); *B29C 66/229* (2013.01); *B29C 66/232* (2013.01); *B29C 66/4722* (2013.01); *B29C 66/7294* (2013.01); *B29C 66/73921* (2013.01); *B29C 66/81427* (2013.01); *B29C 66/81435* (2013.01); *B29C 66/836* (2013.01); *B29C 66/83411* (2013.01); *A61F 2013/15869* (2013.01); *B29C 65/7841* (2013.01); *B29C 66/71* (2013.01); *B29L 2031/4878* (2013.01); *B29L 2031/729* (2013.01)

(58) Field of Classification Search
  CPC .......... B29C 66/7294; B29C 66/73921; B29C 66/81427; B29C 66/81435; B29C 66/83411; B29C 66/836; A44B 18/0065; A61F 13/15739; A61F 13/15756; A61F 13/625
  USPC ...................................................... 156/73.1
  See application file for complete search history.

(56) References Cited

U.S. PATENT DOCUMENTS

2005/0209076 A1    9/2005  Boutron et al.
2016/0143792 A1*   5/2016  Peiffer ................. B29C 65/087
                                                428/99

FOREIGN PATENT DOCUMENTS

EP      2 815 733      12/2014
JP      2011-15796      1/2011
WO      2014/204829    12/2014

* cited by examiner

METHOD FOR MANUFACTURING CLOSING SYSTEMS FOR HYGIENE ARTICLES, IN PARTICULAR DIAPER CLOSING SYSTEMS

FIELD OF THE INVENTION

The invention relates to a method for producing closing systems for hygiene articles, in particular diaper closing systems. An attachment part is fed to the rear face of a support part having projecting closing elements arranged in rows at a predefined distance from each other. The attachment part is joined to the support part along welding points using an ultrasonic welding process. The invention furthermore relates to a connection part, in particular for a hygiene article, such as a baby diaper or incontinence diaper, as well as a hygiene article of this sort.

BACKGROUND OF THE INVENTION

Baby diapers or incontinence diapers designed for a single use have closing systems that permit rapid and simple closing and opening of the diaper, and have attachment parts mounted on the side of the diaper. The attachment parts are in the form of a band or in a wide form called diaper tabs. Support parts connected to the attachment parts comprise projecting closing elements, which in the closed state of the closing system form adhesive connections with the diaper. When producing these closing systems, which have several material layers, for example of non-woven materials, the state of the art forms connection points between the layers by adhesive connections or by welding connections such as ultrasonic welding. The replacement of adhesive connections with welding connections, such as ultrasonic welding, as is disclosed in document EP 2 564 822 B1 for the production of connections between plastic films of diaper closing systems, has the advantage compared with the formation of adhesive connections that used diapers can be easily disposed of because no adhesive materials that compromise the biodegradability are present. Also the risk of damage to the health of the diaper wearer due to toxicity of the adhesive is also avoided, which represents a particular advantage in particular in the case of baby diapers.

The use of the ultrasonic welding process in the case of closing systems in which a support part provided with closing elements is to be connected to an attachment part is problematic in that the heat effect occurring in the welding region on the projecting adhesive closing elements leads to their deformation in the welding region. This deformation is associated with a loss of adhesive force, which compromises the reliability of the diaper closure formed by the closing element. To minimize the loss of adhesive force, one is thus compelled to form only punctiform welding joints, which on the one hand compromises the secure connection between the support part and the attachment part and which is on the other hand complex from a production perspective.

SUMMARY OF THE INVENTION

In light of these issues, the invention addresses this problem by an improved method for producing closing systems for hygiene articles that permits the reliable connection of the support part and the attachment part by ultrasonic welding without compromising the closure properties of the closing system.

According to the invention, this problem is basically solved by a method having, as a significant feature of the invention, at least a portion of the welding points introduced along welding connection lines being between adjacent rows of closing elements and extending at least partially parallel to those rows. Because the welding points extend between adjacent rows of closing elements and the heat effect on the intermediate regions between the closing elements is then limited, the loss of adhesive force is avoided on the one hand. By welding connection lines extending parallel to the closing element rows a welding connection with a relatively large surface area can be produced on the other hand, so that a reliable fastening between the support part and the attachment part is ensured.

The welding process can particularly advantageously be carried out in such a way that at least an anvil part of an ultrasonic welding unit for obtaining the respective welding connection line between the intervals of adjacently arranged rows of closing elements and extending parallel to those rows is brought into an engagement and that the sonotrode cooperating with the respective anvil part comes into contact with that side of the attachment part that faces away from the connection elements.

In a particularly advantageous manner, the respective anvil parts may be used as a component of a block tool or disk tool, with several anvil parts held at a predefinable spacing adjusted to the row distance between the closing elements of the support part extending parallel to one another form parts of the block tool or disk tool. This structure permits simultaneously forming, in a particularly economical manner by relative movement between the material sheets and the block tool or disk tool, a plurality of welding connection lines and then a connection region with a large surface area.

In advantageous embodiments, to obtain a guide for the support part, which for a welding process is moved together with the attachment part along the block tool, anvil parts serving as guide strips are used on the block tool. The guide strips engage in the spacings between the adjacent rows of closing elements, preferably with partial reaching under same. The guide additionally formed by the anvil parts permits carrying out a particularly reliable welding process without compromising the closing elements.

For obtaining a guide for the support part, which is moved for a welding operation together with the attachment part along the preferably rotatably arranged disk tool, advantageously, in the movement direction in front of and/or behind the disk tool, guide parts are arranged, which position the rows of closing elements for a defined engagement of the respective anvil part of the disk tool between the assignable rows of closing elements.

The closing elements of the support part are preferably arranged in rows both in the longitudinal direction and in the transverse direction. The spacing between the closing elements both in the longitudinal direction and in the transverse direction remain the same.

The respective welding connection lines between the support part and the attachment part are each introduced such that the closing elements of the support part are welded in a damage-free manner to the attachment part.

With regards to the formation of the closing elements forming an adhesive closure, in addition to locking hooks or loops, closing heads are particularly preferably used. The closing heads project by shaft parts on the top side of the support part and are formed projecting at least partially over the shaft parts at the end forming a locking opportunity for correspondingly formed closing elements of an additional support part.

As disclosed in DE 196 46 318 A1, the support part can be formed integral with its closing elements, with the attachment part being formed from a non-woven and with thermoplastic plastic materials, such as polyolefins or polyamide (PA12), being used for both parts.

The attachment part can be formed projecting at the edge at least partially over the welded-on support part with the closing elements. The respective projecting part of the attachment part is used at least partially as a connection part for the corresponding hygiene article, such as a baby diaper or incontinence diaper. The projecting part of the attachment part opposite the connection part can be used as a grip tab for easy opening of the corresponding diaper closure.

Another subject of the invention is a connection part, in particular for a hygiene article, such as a baby diaper or incontinence diaper.

Another subject of the invention is, a hygiene article, which comprises at least one connection part.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure.

DETAILED DESCRIPTION OF THE INVENTION

Figure 1:
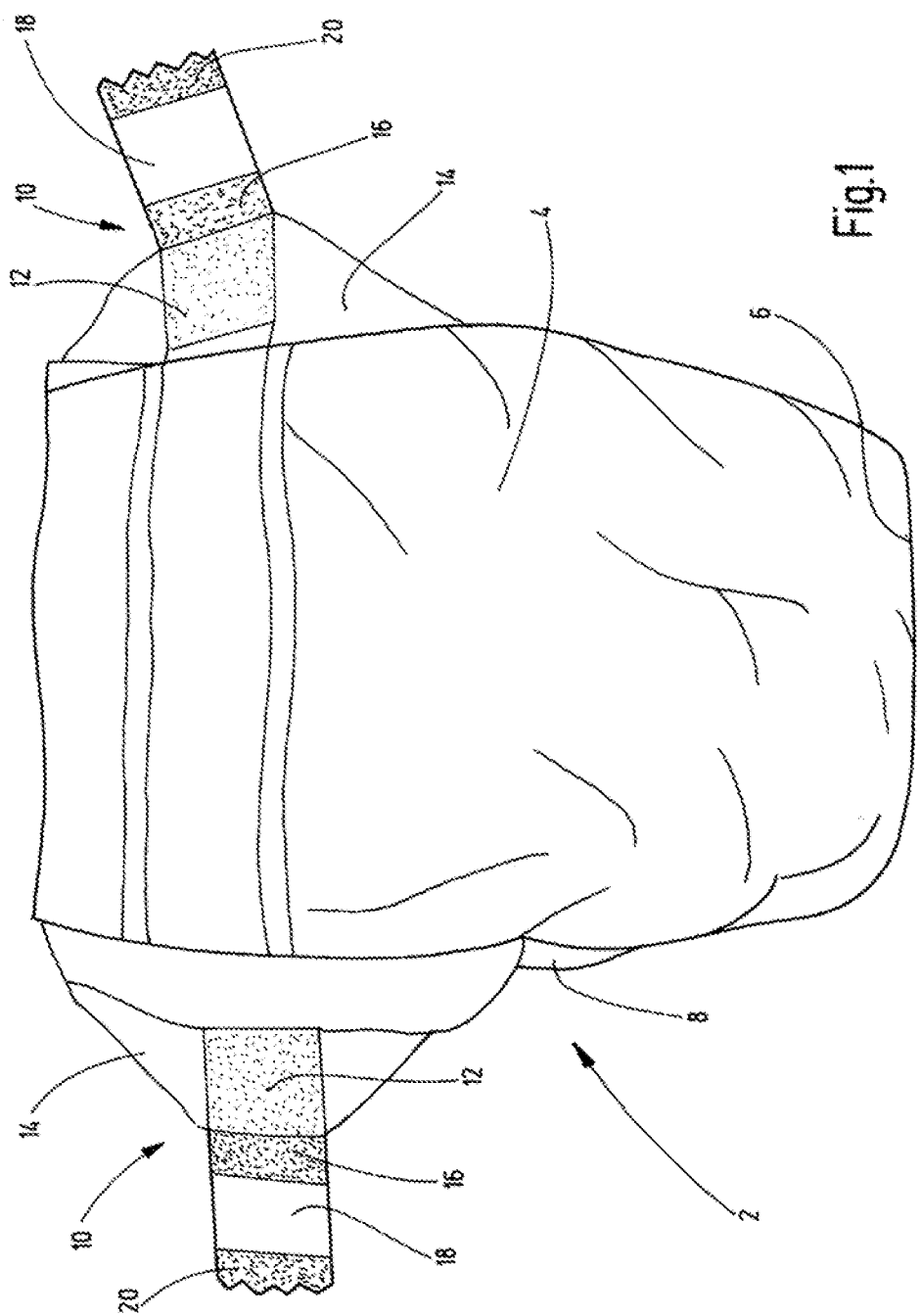
FIG. 1 is a schematic top view of a baby diaper with a closing system depicted in the opened state and produced according to a method according to an exemplary embodiment of the invention.

FIG. 1 shows a baby diaper 2 intended for a single use with the viewing direction of the diaper front side 4, which lies around the edge region 6 lying at the bottom in FIG. 1 and which lies on the diaper rear side 8. The closing system, which is depicted in FIG. 1 in the opened state, has connection parts 10. Each part 10 is formed by the exposed section of a band-shaped attachment part 16, which with its end section 12 is mounted on a step 14 that, in the form of diaper tabs, are located on both sides of the diaper rear side 8. The attachment parts 16 are formed from a non-woven made of thermoplastic plastic material, such as a polyolefin, polyester or polyamide (PA12). The steps 14 likewise are made of a corresponding thermoplastic material with good welding properties, so that the connection of the end sections 12 to the steps 14 is advantageously formed by welding.

On the section of the attachment part 16 projecting over the respective step 14, a support part 18 provided with projecting closing elements is located at a distance from the section 20 located at the free end. Section 20 forms a gripping lug that can be grasped by the user. The support part 18 has closing elements projecting on the top side, which closing elements are only visible in FIGS. 2, 4 and 6 and are partially numbered therein with the number 22. In the closed state of the closing system when the connection parts 10 are laid around the diaper front side 4, closing elements 22 form an adhesive connection with closing elements on another support part. The adhesive force of the adhesive connection secures the closing system in the closed state.

Figure 2:
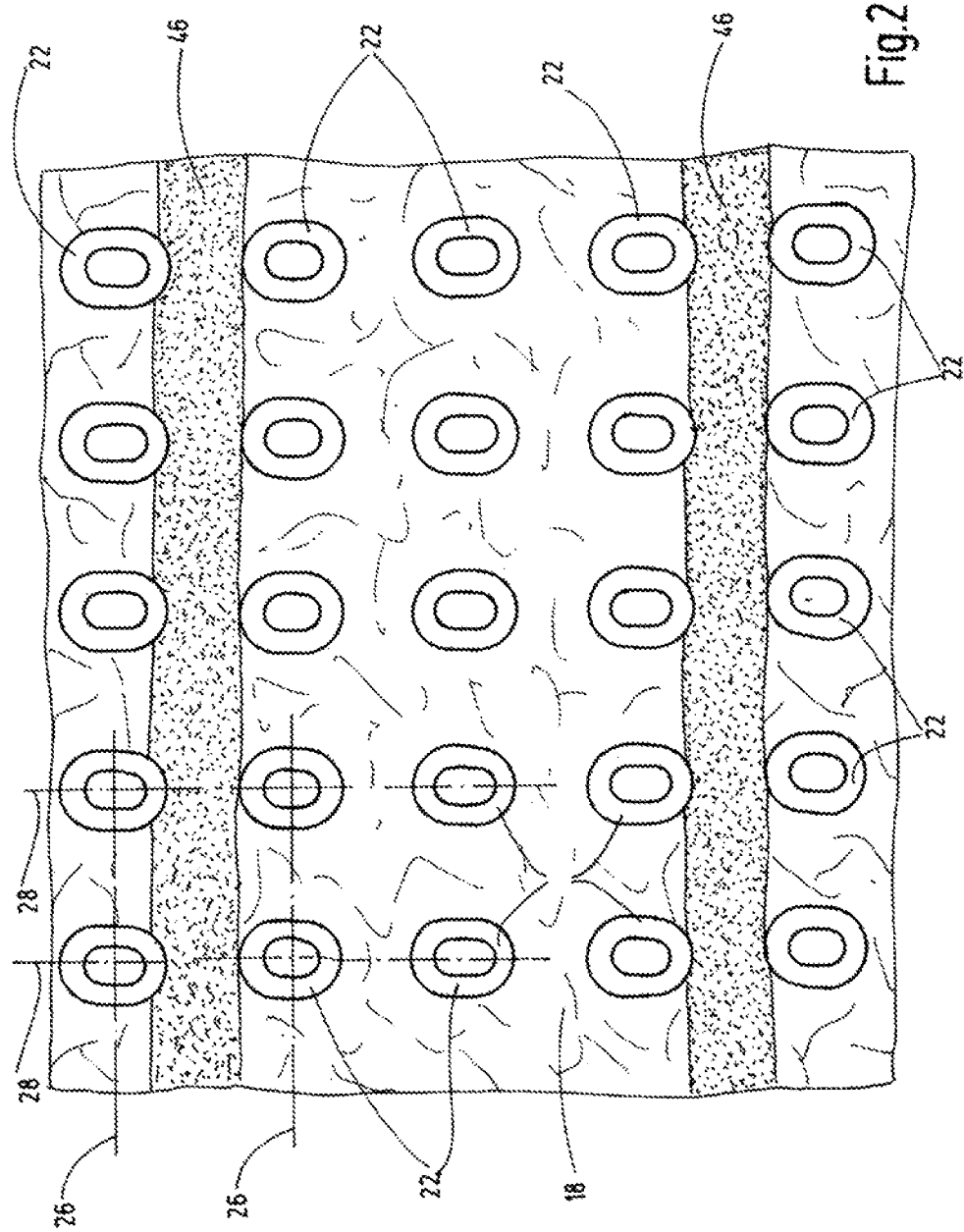
FIG. 2 is a partial top view of the support part of the closing system, magnified approximately 50 times according to an exemplary embodiment of the invention.
Figure 4:
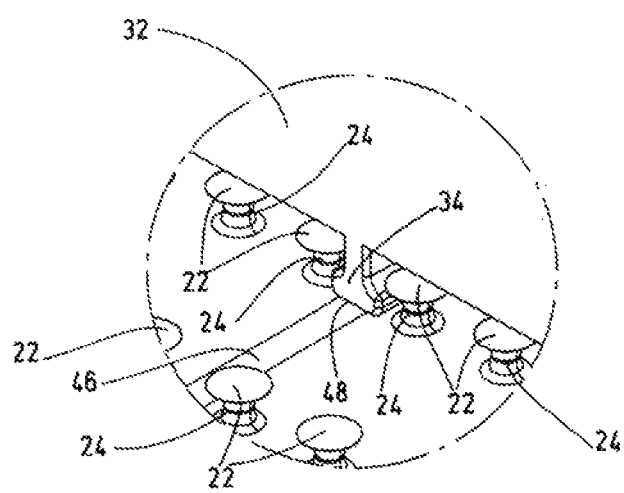
FIG. 4 is a magnified, partial perspective view of the region identified with IV in FIG. 3, of an ultrasonic welding device for carrying out the production method according to the invention.

As FIGS. 2 and 4 most clearly show, the closing elements 22 have closing heads, which are formed in the manner of a mushroom head and which are integrally connected via shaft parts 24 (FIG. 4) to the non-woven of the support part 18. The closing heads can be formed round, oval or polygonal, in particular hexagonal. The support part 18 can be produced for example from a polyolefin, a polyester or from polyamide (PA12) together with the closing elements 22 in one work step by a device as disclosed in document DE 196 46 318 A1, in a continuous method. The thermoplastic plastic material is fed to the gap between a pressure roller and a shaping roller, which has a screen with open cavities giving the closing elements 22 their form. The closing elements are arranged in straight rows of lines 26 and columns 28 perpendicular to the rows, as is depicted in FIG. 2. As can also be seen from this figure, the closing elements 22 have in the direction of the lines 26 the same spacing from one another, which corresponds to the relative distances, viewed in the direction of the columns 28, so that the regular pattern of the closing elements 22 depicted in FIG. 2 is formed.

Figure 3:
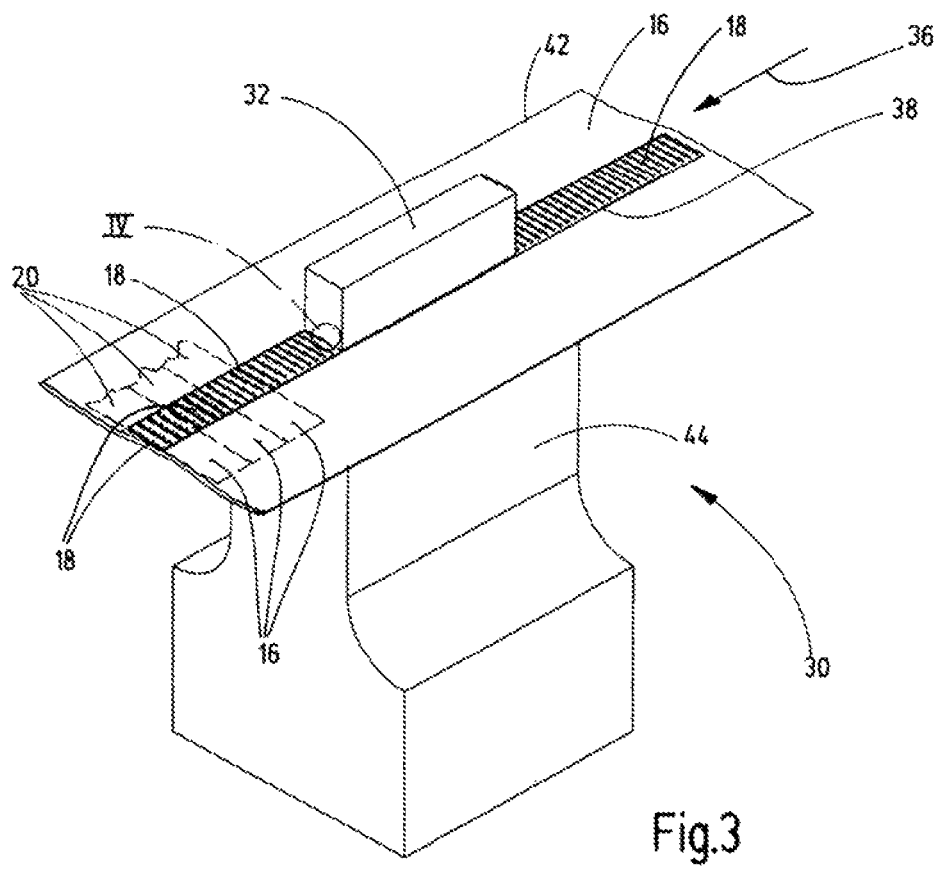
FIG. 3 is a schematically simplified, perspective view of an ultrasonic welding device for carrying out the method, according to a first exemplary embodiment of the invention, for production of the closing system.

FIGS. 3 and 4 show a first exemplary embodiment of the production method according to the invention. For the formation of the welding connection between the support part 18 and the attachment part 16 an ultrasonic welding unit 30 is used, which welding unit has anvil parts 34 located in a block tool 32, of which only one is visible in FIG. 4. In an advancement direction 36 shown in FIG. 3 with an arrow 36, a semi-finished part, from which after the realized welding operation the individual connection parts 10 are separated, a non-separated sheet 42 of the attachment part 16 with a strip 38 laying thereon of the prefabricated support part 18 is passed below the anvil parts 34 of the block tool 32 between block tool 32 and a sonotrode 44. The sonotrode surface extends over the length of the block tool 32 measured in the advancement direction. The anvil parts 34, which likewise extend over this length of the block tool 32, are arranged in the direction extending perpendicular to the advancement direction at such distances from one another that after three lines 26 (FIG. 2) of the closing elements 22 they are aligned with a row extending in the advancement direction. The welding connection lines identified in FIG. 2 with the reference numeral 46 are then formed. As indicated in FIG. 3 with dotted and dashed lines, after the welding operation has been realized, the finished connection parts 10 are separated from the sheet 42.

The precise positioning of the welding connection lines 46 in the gap between adjacent closing elements 22, which means that the thermal deformation thereof during the welding operation is prevented, takes place in this embodiment by a guide function realized by the anvil parts 34, which extend as guide strips along the entire length of the block tool 32 measured in the advancement direction and slide without rotating on the support part front surface from which the closing element 22 projects. As FIG. 4 shows, the anvil parts 34 have for their guiding function a cross section in the form of an upside-down T, the end crossbar 48 of anvil parts reaches under the heads of adjacent rows of the closing elements 22, so that the crossbars 48 form side guiding surfaces for the shafts 24 of the closing elements 22 of the assigned rows.

As particularly shown in FIG. 4, the anvil parts are T-shaped with axial sections and transverse sections. The axial sections extend between the locking hooks or closing heads. The transverse sections extend between the locking hooks or closing heads and the front face of the support part in directions parallel to the longitudinal axes of the shaft part 24, with the transverse sections having widths in directions transverse to a direction of the guiding movement greater than spacings of the locking hooks or closing heads in adjacent rows.

Figure 5:
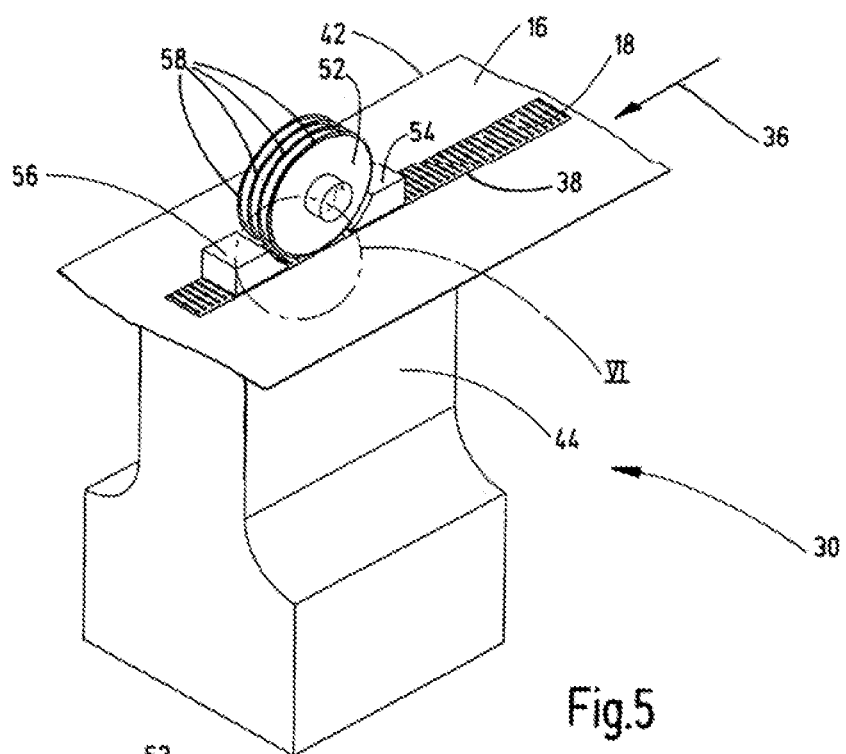
FIG. 5 is a schematically simplified perspective view of an ultrasonic welding device for carrying out the production method according to a second exemplary embodiment of the invention.
Figure 6:
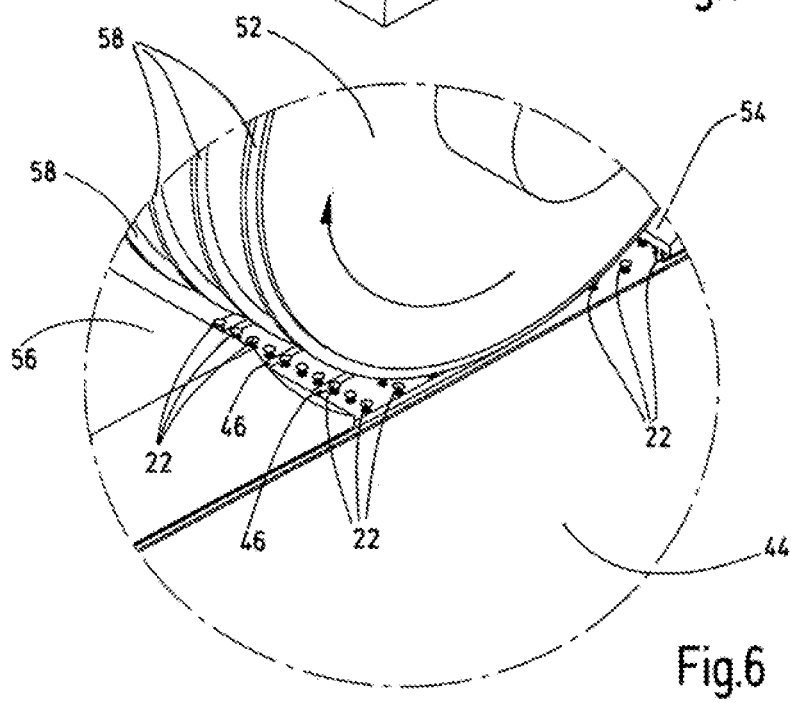
FIG. 6 is a magnified, partial perspective view of the region of the welding device identified with VI in FIG. 5.

In the embodiment of FIGS. 5 and 6, an ultrasonic welding unit 30 is used, in which, with an otherwise identical unit construction, instead of a block tool 32 having the anvil parts 34, a disk tool 52 is used. Viewed in the advancement direction, immediately in front of and behind the disk tool 52, guiding parts 54 and 56 are arranged. Guiding parts 54, 56 take over the guiding function, which in the welding unit 30 of FIGS. 3 and 4 is realized by the anvil parts 34. These guiding parts 54 and 56 have, on the bottom side not visible in the drawing, projecting guide ribs, which in a corresponding manner to that shown in FIG. 4 for the anvil parts 34, realize the guiding function by reaching under the heads on the shafts 24 of adjacent rows of closing elements 22.

On the external circumference of the disk tool 52, anvil parts 58 are provided by radially projecting ribs continuously extending in the circumferential direction. In the rotational movement of the disk tool 52 occurring in the advancement movement of the sheet 42 and the strip 38, anvil parts roll out between corresponding rows of adjacent closing elements 22, and then generate the welding connection lines 46 together with the surface sonotrode 44 in the same way as in the embodiment of FIGS. 3 and 4. With the respective annular anvil part 58, which can be formed rotating about its longitudinal axis, very high contact and welding forces can be generated due to the smaller working surface with the medium to be welded compared with the block tool 32. The rotation speed of the disk tool 52 as the anvil for the sonotrode 44 is also adapted to the advancement speed of the sheet 42 and the strip 38.

The formation of the welding connection lines 46 in the direction of lines 26 (cf. FIG. 2), which extend in the advancement direction of the corresponding ultrasonic welding unit 30, has the advantage that the welding operation can take place in continuous advancement, which permits particularly economical production of the connection parts 10. Alternatively however, possibly in the case of a discontinuous welding operation, welding connection lines could also be formed in the direction of the strips 28 or alternately in both directions. Although in the examples shown in the figures closing elements 22 are provided with mushroom heads located on shafts 24, it shall be understood that with correspondingly formed additional support parts forming the adhesive connection with the support parts 18, which are located for example on the diaper front side 4, differently formed closing elements such as hooks or loops can be used.

It is within the scope of the invention to form the respective anvil part 34 or 58 as a sonotrode and to operate the sonotrode 44 as an anvil of the ultrasonic welding unit 30.

While various embodiments have been chosen to illustrate the invention, it will be understood by those skilled in the art that various changes and modifications can be made therein without departing from the scope of the invention as defined in the claims.

The invention claimed is:

1. A method for producing closing systems for hygiene articles, the method comprising the steps of:
   providing a support part having projecting closing elements arranged in rows at a predefined distance from each other on a front face of the support part and having a rear face of the support part;
   feeding an attachment part to the rear face of the support part;
   ultrasonically welding process the attachment part to the support part along welding lines between and parallel to adjacent rows of the closing elements by anvil parts and a sonotrode part of an ultrasonic welding unit, the anvil parts being engaged in spacings between and being arranged parallel to the adjacent rows of the closing elements, the sonotrode cooperating with the anvil parts and contacting a side of the attachment part facing away from the closing elements, the anvil parts being components of a block tool, being spaced by a distance from one another by distances corresponding to spacings of the rows of the closing elements on the support part and being parallel to one another; and
   guiding movement to the support part with the attachment part relative to the block tool during the ultrasonic welding by the anvil parts serving as guide strips and engaging in the spacings between the adjacent rows of closing elements.

2. A method according to claim 1 wherein
   the block tool is located at least one of in front of or behind a tool disk in a movement direction of the movement of the support part and the attachment part relative to the block tool to guide the tool disk in the spacings between the adjacent rows of the closing elements.

3. A method according to claim 2 wherein
   the tool disk rotates relative to the block tool.

4. A method according to claim 1 wherein
   the closing elements are arranged on the support part in a longitudinal direction and a transverse direction in the rows and in columns, respectively, and are spaced by equal distances in the longitudinal direction and in transverse direction.

5. A method according to claim 1 wherein
   the welding lines between and connecting the support part and the attachment part are formed without damage to the closing elements.

6. A method according to claim 1 wherein
   the closing elements have at least one of locking hooks or closing heads projecting axially and radially from ends of shaft parts on the front face of the support part, with the ends of the shaft parts bring remote from the support part, the at least one of the locking hooks or closing heads being capable of locking with corresponding closing elements of an additional support part.

7. A method according to claim 1 wherein
   the support part is formed integrally with the closing elements and is formed of thermoplastic materials; and the attachment part is formed of a non-woven of thermoplastic material.

8. A method according to claim 7 wherein
the thermoplastic material is at least one of a polyolefin, polyester or polyamide.

9. A method according to claim 1 wherein
the attachment part projects at a side at least partially over the support part welded thereon, with a projecting part of the attachment part being a connection part on a hygiene article.

10. A method according to claim 9 wherein
the hygiene article is a baby or incontinence diaper.

11. A method according to claim 6 wherein
the anvil parts are T-shaped with axial sections and a transverse sections, the axial sections extending between the at least one of the locking hooks or closing heads, the transverse sections extending between the at least one of the locking hooks or closing heads and the front face of the support part in directions parallel to the longitudinal axes of the shaft parts with the transverse sections having widths in directions transverse to a direction of the guiding movement greater than spacings of the at least one of locking hooks or closing heads in the adjacent rows.

12. A method according to claim 1 wherein
the block tool slides along the front surface of the support part without rotating.

13. A method according to claim 1 wherein
the anvil parts have planar surfaces that slide along the front surface of the support part without rotating.

* * * * *